United States Patent [19]
Lansink-Rotgerink et al.

[11] Patent Number: 5,773,677
[45] Date of Patent: Jun. 30, 1998

[54] PROCESS FOR THE HYDROGENOLYSIS OF C—O AND C=O BONDS IN ORGANIC SUBSTANCES

[75] Inventors: Hans Lansink-Rotgerink, Glattbach; Mario Scholz, Gruendau; Andreas Freund, Kleinostheim; Guenther Kunz, Bruchkoebel, all of Germany

[73] Assignee: Degussa Aktiengesellschaft, Frankfurt am Main, Germany

[21] Appl. No.: 715,775

[22] Filed: Sep. 19, 1996

[30] Foreign Application Priority Data

Sep. 23, 1995 [DE] Germany ................. 195 35 395.1

[51] Int. Cl.⁶ .................................................. C07C 1/20
[52] U.S. Cl. ............................................................ 585/469
[58] Field of Search ................................................ 585/469

[56] References Cited

U.S. PATENT DOCUMENTS 2,297,769 10/1942 Ipatieff et al. ........................ 260/668
3,944,627 3/1976 Schram et al. ........................ 260/668

FOREIGN PATENT DOCUMENTS 904529 2/1954 Germany .
2424708 5/1973 Germany .

OTHER PUBLICATIONS

Chemical Abstracts, vol. 114 (May 13, 1991), No. 19, XP000121966, JP 02273630.

*Primary Examiner*—Samuel Barts
*Attorney, Agent, or Firm*—Beveridge, DeGrandi, Weilacher & Young, L.L.P.

[57] ABSTRACT

A process for hydrogenolysis of C—O and C=O bonds in organic substances by reaction with hydrogen in the presence of a catalyst system which contains at least one metal from Groups VIII and/or IB of the Periodic System of Elements on a support consisting of at least one solid acid with an acid activity index of at least 90%.

16 Claims, No Drawings

PROCESS FOR THE HYDROGENOLYSIS OF C—O AND C=O BONDS IN ORGANIC SUBSTANCES

INTRODUCTION AND BACKGROUND

The present invention relates to a process for the hydrogenolysis of C—O and C=O bonds in organic substances by reaction with hydrogen in the presence of a catalyst system. The organic substances are preferably compounds of the type I or II with the following structural formulae:

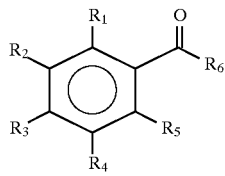

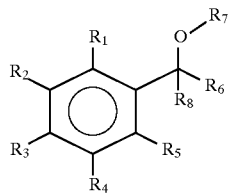

Hydrogenolysis of the C=O or C—O bonds produces compounds of the type III or IV:

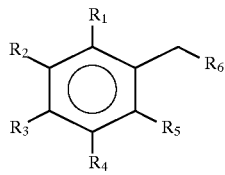

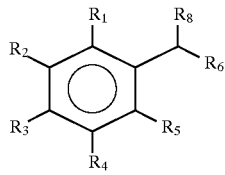

To perform these reactions, compounds of the type I or II have hitherto been placed in contact with molecular hydrogen or a hydrogen donor in the presence of a solid hydrogenation catalyst in a mixture of a solvent and a liquid acid.

As described in U.S. Pat. No. 5,124,489, the hydrogenation catalyst generally contains a metal from group VIII, such as e.g. Pd, Pt or Ni. This metal is frequently applied to a catalyst support. Suitable catalyst supports are aluminum oxide, silicon dioxide and activated carbon. In particular, the combination consisting of Pd on activated carbon (Pd/C) is frequently used for these reactions.

Further examples of this type of reaction are given in U.S. Pat. No. 5,047,592 (examples 1 and 2). In these examples, 10 wt. % Pd/C is used as the hydrogenation catalyst and dilute hydrochloric acid is mentioned as the acid. Other examples, in which acetals are reacted in the presence of hydrochloric acid and 5 or 10 wt. % Pd/C catalyst, are described in U.S. Pat. No. 5,124,489 (examples 2, 3, 4, 5, 7 and 9).

According to the prior art, the liquid acid may be an inorganic acid, an organic acid or a Lewis acid. Examples are sulphuric acid, hydrochloric acid, phosphoric acid, acetic acid, formic acid, benzenesulphonic acid, toluenesulphonic acid, methanesulphonic acid, aluminum trichloride, etc. Due to the presence of these acids, it is essential to work in an expensive, corrosion-resistant unit. In addition, an acid-containing effluent stream is produced after termination of reaction and this has to be disposed of.

The reaction products are frequently obtained as salts when using the acids mentioned above.

An object of the present invention is to provide a process for the hydrogenolysis of C—O or C=O bonds in organic substances which does not require the use of corrosive media and thus greatly simplifies the disposal procedure for the effluent streams. In addition, the catalytic activity and selectivity are intended to be improved when compared with processes known from the prior art.

SUMMARY OF THE INVENTION

The above and other objects are achieved in accordance with the invention by a process for the hydrogenolysis of compounds of the type I or II to give compounds of the type III or IV by reaction with hydrogen in the presence of a catalyst system, namely, a solid catalyst which contains at least one metal from Group VIII and/or IB of the Periodic System of Elements on a carrier consisting of at least one solid acid with an acid activity index of at least 90%.

DETAILED DESCRIPTION OF INVENTION

The present invention has substantial advantages as compared with the prior art described above. The process may be performed very effectively without the addition of liquid acids. This minimizes corrosion problems in the plant. There is no need to dispose of acids. Also, the reaction product is not obtained as a salt. In addition, the catalyst system according to the invention can be repeatedly recycled, i.e. it may be used several times.

In compounds of the type I, II, III and IV, the substituents $R_1$ to $R_8$, independently of each other, may be hydrogen (H), alkyl groups, substituted or non-substituted aryl groups, hydroxyl groups, alkoxy groups, substituted or non-substituted aryloxy groups, halogen groups, carboxylic acid groups, carboxylic acid derivative groups, acyloxy groups, nitro groups, sulphonic acid groups, mercapto groups, amino groups, alkyl-substituted amino groups and substituted or non-substituted aryl-substituted amino groups. In the case of alkyl groups, these may contain 1 to 20 carbon atoms, preferably 1–6 carbon atoms. In the case of substituted or non-substituted aryl groups, these preferably are phenyl groups.

In accordance with the invention described here, compounds of the type I or II either diluted or dissolved in a solvent without additional liquid acid are placed in contact with the solid catalyst in a reactor. Hydrogen is introduced or added either as molecular hydrogen or in the form of a hydrogen donor.

The solid catalyst contains at least one hydrogenating metal and at least one acid component. The acid component acts both as a solid acid and as a support for the hydrogenating metal. Suitable hydrogenating metals are metals from Groups VIII (Fe, Co, Ni, Ru, Rh, Pd, Os, Ir and Pt) and IB (Cu, Ag and Au). Preferably, however, Rh, Pd, Pt or Ni are used. Good results are obtained in particular when using Pd. The catalytic effect of the hydrogenating metal or hydrogenating metals may be modified by the addition of promoters. Elements from group IVA (Sn, Ge, Pb) or indium, for example, may be used as promoters.

The metal content may be between 0.01 and 90 wt. %, with respect to the total weight of catalyst. When using noble metal catalysts the preferred metal content is in the range between 0.01 and 30 wt. %. In the case of base metal catalysts, the metal content may be much higher. When using a co-precipitated nickel/aluminum oxide catalyst, for example, good metal dispersions are obtained with metal contents of up to 90 wt. % (H. G. J. Lansink-Rotgerink et al. in Applied Catalysis, vol. 27, (1986), page 41). The catalyst may be initially introduced in its reduced form or be reduced in-situ while the process according to the invention is being performed.

The acid component acting as a support for the hydrogenating metal in the catalyst is a solid acid with an acid activity index of at least 90%. The acid activity index is determined in a test in which a gas stream, consisting of 5 vol. % of isopropanol and 95 vol. % of helium, is passed through a catalyst bed. The amount of catalyst in the reactor is 1.00 g, the catalyst consisting of particles in the range 0.5–2.0 mm. The rate of flow of helium through the reactor is 50 ml/min. The isopropanol is decomposed by the solid acid. Propene and water are then produced as the primary main products. Secondary products may be formed, depending on the solid acid. The acid activity index in the context of this invention is defined as the degree of conversion of isopropanol at a temperature of 250° C.

To perform the process according to the invention, an acid activity index in the vicinity of 100% is desirable for the catalyst support. The activity of the catalyst for hydrogenolysis of C—O and C=O bonds decreases rapidly with decreasing acid activity index. If the acid activity index is below 90%, the process ceases to be economically viable.

Examples of solid acids are: amorphous mixed oxides which contain silicon and aluminum and crystalline compounds based on Si, Al and O. The compounds may be modified in a known manner by soaking them with acids. Sulphuric or phosphoric acid are suitable, for example, for modifying the acid supports.

The compounds mentioned comprise only a small selection of suitable solid acids. For a review of the field of solid acids, reference is made to the book, Studies in Surface Science and Catalysis, vol. 51, (New Solid Acids and Bases) by K. Tanabe et al. (Elsevier Science Publishers, Amsterdam, 1989).

The $SiO_2/Al_2O_3$ molar ratio in the amorphous Si/Al mixed oxides may vary from 99:1 to 1:99, preferably 95:5 to 5:95.

The crystalline compounds based on Si, Al and O include the group of zeolites such as, for example, ZSM-5, mordenite, zeolite-beta or zeolite-Y. The $SiO_2/Al_2O_3$ molar ratio in the zeolites may vary from 2 to infinity. The zeolites are preferably used in the H-form.

The process according to the invention is performed at temperatures between −20° and 500° C. If molecular hydrogen is used, the hydrogen pressure varies between 0.1 and 100 bar, depending on the type of reactant. Hydrogen may also be supplied in-situ via a hydrogen donor.

Reaction may be performed either in a batch process, in a semi-continuous process or in a continuous process. The process may be performed either in suspension or in a fixed bed. In the former case, the catalyst is present as a powder, in the latter case as solid granules with dimensions of at least 0.3 mm. In the case of a fixed bed process, reaction may take place either in the liquid phase, in the gas phase or in a supercritical phase.

The water produced during reaction may optionally be eliminated by adsorption or by use of a water separator, e.g. a Dean separator.

The following examples will serve to illustrate the invention.

EXAMPLE 1

To perform the process according to the invention, palladium catalysts, each with 2 wt. % of palladium, were prepared on different support materials. For this, the support materials were impregnated with a solution of palladium chloride, filtered off, washed chlorine-free, dried, calcined at 400° C. under an atmosphere of nitrogen and then reduced in a stream of forming gas (5 vol. % $H_2$, 95 vol. % $N_2$) at 400° C. The reduced catalysts were stored dry in air.

Catalysts A to D, prepared in this way, are characterized in Table 1 which gives data on the support materials, the residual $Na_2O$ content, the molar ratio of $SiO_2/Al_2O_3$ and the acid activity index measured.

Table 1 also includes Catalyst E, a commercial palladium catalyst on activated carbon, which was used in the following process examples to enable comparison with the process according to the prior art.

TABLE 1

Palladium catalysts (2 wt. % Pd) on different support materials

| Catalyst | Material | Support |  |  |
|---|---|---|---|---|
|  |  | $Na_2O$ [wt.-%] | $SiO_2/Al_2O_3$ [mol/mol] | Acid activity [%] |
| A | ZSM-5; H-form | 0.01 | 27.4 | 100 |
| B | Mordenite H-form | 0.4 | 29.6 | 100 |
| C | Zeolite-Beta H-form | 0.05 | 27 | 100 |
| D | Zeolite Y H-form | 0.1 | 27.4 | 100 |
| E | 5 wt.-% Pd/C; | commercial catalyst for comparison tests | | |

EXAMPLE 2

The process according to the invention was tested by way of example in the reaction of 1-phenylethanol with hydrogen to give ethylbenzene, using catalysts A to D. For this purpose, 5 g of 1-phenylethanol (corresponding to 40.93 mmol) were diluted with 115 ml of ethanol and, along with the catalyst, placed in a reactor filled with hydrogen gas. The amount of catalyst used each time was such that 100 mg of palladium were available in the reactor for hydrogenation.

Catalyst E was used to convert 1-phenylethanol to ethylbenzene with hydrogen in accordance with the known process from the prior art. Again, the amount of catalyst used was such that 100 mg of palladium were available in the reactor for hydrogenation. In this case, 12 ml of a 46 wt. % sulphuric acid as a liquid acid were added to the reaction mixture. Without the addition of acid, no significant conversion of 1-phenylethanol occurred with catalyst E.

Reaction was performed at 30° C. at a hydrogen pressure of 1.01 bar (abs.), with continuous stirring. In each case, the reaction was terminated after 5 hours, the catalyst was isolated from the reaction mixture and the reaction mixture was analyzed by means of gas chromatography, using a FID detector. The results are summarized in Table 2. The percentages cited in Table 2 refer to the percentage by area of the relevant substance after subtracting the solvent peak.

As can be seen from Table 2, catalysts A to D, even without the addition of acid, are much more active and selective during the conversion of 1-phenylethanol to give ethylbenzene than is catalyst E with added acid.

TABLE 2

Hydrogenolysis of 1-phenylethanol with catalysts A to E

| Catalyst | Type | Acid added | 1-phenyl-ethanol [Area-%] | Ethyl-benzene [Area-%] | Aceto-phenone [Area-%] | Ethyl ether of 1-phenyl-ethanol [Area-%] |
|---|---|---|---|---|---|---|
| A | 2% Pd, ZSM-5 | no | 29.7 | 69.9 | 0.4 | 0.0 |
| B | 2% Pd, MOR | no | 12.8 | 87.0 | 0.2 | 0.0 |
| C | 2% Pd, BETA | no | 6.5 | 93.0 | 0.3 | 0.2 |
| D | 2% Pd, Y | no | 4.7 | 94.4 | 0.6 | 0.3 |
| E | 5% Pd, C | yes | 3.0 | 73.2 | 23.4 | 0.4 |

MOR: mordenite; BETA: zeolite-beta; Y: zeolite-Y

EXAMPLE 3

In the same way as in example 1, two further palladium catalysts were prepared on zeolite-beta (H-form, $Na_2O$ content: 0.05 wt. %, $SiO_2/Al_2O_3$=27 mol/mol, acid activity index 100%). The amount of palladium applied was varied. All the other parameters were identical to those in example 1.

Catalyst F obtained in this way contained 5 wt. % of palladium and catalyst G contained 20 wt. % of palladium.

EXAMPLE 4

Catalysts C, F and G were used to hydrogenolyze 1-phenylethanol in the same way as in example 2. The amount of Pd used, as in example 2, was 100 mg each time, i.e. the amount of catalyst for catalysts F and G were reduced in accordance with their palladium content. The results are summarized in Table 3.

TABLE 3

Hydrogenolysis of 1-phenylethanol using catalysts C, F and G

| Catalyst | Pd [Wt.-%] | 1-phenyl-ethanol [Area-%] | Ethyl-benzene [Area-%] | Aceto-phenone [Area-%] | Ethyl ether of 1-phenyl-ethanol [Area-%] |
|---|---|---|---|---|---|
| C | 2 | 6.5 | 93.0 | 0.3 | 0.2 |
| F | 5 | 8.4 | 88.8 | 2.8 | 0.0 |
| G | 20 | 11.7 | 86.4 | 1.7 | 0.2 |

As can be seen from Table 3, both the activity and the selectivity towards the desired product decrease slightly with increasing palladium content. The activity and the selectivity, however, remain well above those for the conventional process using catalyst E.

EXAMPLE 5

It was attempted to convert 1-phenylethanol with catalyst F without using hydrogen. The test was performed in the same way as in example 2, but nitrogen was used to flush out the reactor instead of hydrogen. The results are given in Table 4.

TABLE 4

Test results for the hydrogenolysis of 1-phenylethanol using catalyst F Effect of hydrogen

| Catalyst | Gas phase | 1-phenyl-ethanol [Area-%] | Ethyl-benzene [Area-%] | Aceto-phenone [Area-%] | Ethyl ether of 1-phenyl-ethanol [Area-%] |
|---|---|---|---|---|---|
| F | $N_2$ | 80.9 | 8.7 | 10.3 | 0.1 |
| F | $H_2$ | 8.4 | 88.8 | 2.8 | 0.0 |

It can be seen from Table 4 that some of the reactant is converted into the desired product even without the addition of hydrogen. In this case, hydrogen transfer from 1-phenylethanol (H donor) takes place to give ethylbenzene (H acceptor), with simultaneous formation of acetophenone. The conversion and selectivity, however, are much lower than in the presence of gaseous hydrogen.

EXAMPLE 6

In the same way as in example 1, a further palladium catalyst (catalyst H) was prepared on pyrogenic silica (Degussa Aerosil-200; >99 wt. % $SiO_2$). Differently from the supports in example 1, pyrogenic silica has an acid activity index of only about 30%.

Catalyst H was tested in the same way as in example 2. The result is given in the Table below.

TABLE 5

Test results for the hydrogenolysis of 1-phenylethanol using catalyst H

| Catalyst | Type | Acid added | 1-phenyl-ethanol [Area-%] | Ethyl-benzene [Area-%] | Aceto-phenone [Area-%] | Ethyl ether of 1-phenyl-ethanol [Area-%] |
|---|---|---|---|---|---|---|
| H | 2% Pd, $SiO_2$ | no | 89.8 | 9.0 | 0.0 | 0.0 |

As can be seen from the results, catalyst H, with an acid activity index of 30%, has a much lower activity than the other catalysts which were used under the same conditions.

Further variations and modifications of the foregoing will be apparent to those skilled in the art and are intended to be encompassed by the claims appended hereto.

German priority application 195 35 395.1 is relied on and incorporated herein by reference.

We claim:

1. A process for the hydrogenolysis of a compound represented by the structural formula I or II to give a compound represented by the structural formula III or IV

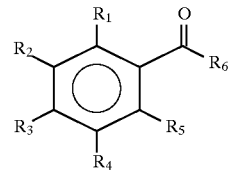

I

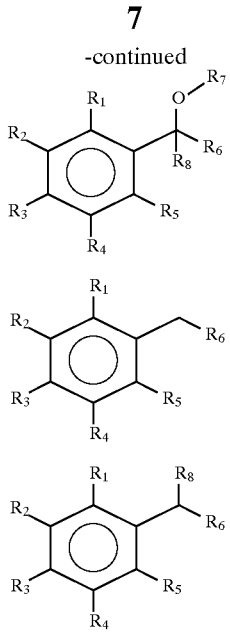

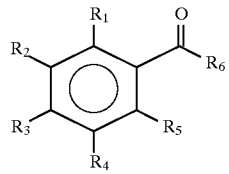

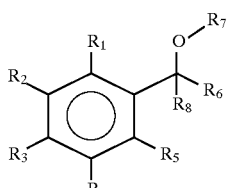

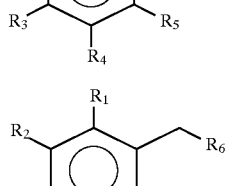

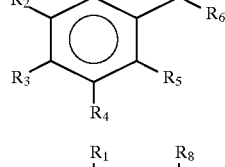

comprising reacting I or II with hydrogen in the presence of a catalyst system that is a solid catalyst which contains at least one metal from Group VIII and/or Group IB of the Periodic System of Elements on a support consisting of at least one solid acid with an acid activity index of at least 90%, wherein the substituents $R_1$ to $R_8$, are the same or different, and are each a member selected from the group consisting of hydrogen, alkyl, substituted or non-substituted aryl, hydroxyl, alkoxy, substituted or non-substituted aryloxy, halogen, carboxyl, a carboxylic acid derivative group, acyloxy, nitro, a sulphonic acid, mercapto, amino, alkyl-substituted amino and substituted or non-substituted aryl-substituted amino.

2. The process according to claim 1, wherein said catalyst contains at least one of the metals selected from the group consisting of palladium, platinum, rhodium and nickel.

3. The process according to claim 1 wherein the solid acid is an amorphous mixed oxide which contains silicon and aluminum or a crystalline compound containing silicon, aluminum and oxygen.

4. The process according to claim 1 wherein the solid acid is a zeolite.

5. The process according to claim 4, wherein the zeolite is ZSM-5, Y, beta or mordenite.

6. The process according to claim 1 wherein a non-zeolitic material is used as the solid acid.

7. The process according to claim 1 wherein at least one mixed oxide is used as a non-zeolitic material.

8. The process according to claim 7 wherein the mixed oxide is modified with an acid.

9. The process according to claim 1 wherein $R_1$ to $R_8$, independently of each other, are hydrogen (H), alkyl groups, substituted or non-substituted aryl groups, substituted or non-substituted phenyl groups, hydroxyl groups, alkoxy groups, substituted or non-substituted aryloxy groups, halogen groups, carboxylic acid groups, carboxylic acid derivative groups, acyloxy groups, nitro groups, sulphonic acid groups, mercapto groups, amino groups, alkyl-substituted amino groups or substituted or non-substituted aryl-substituted amino groups.

10. The process according to claim 1 wherein at least one $R_1$ to $R_8$ is alkyl containing 1 to 20 carbon atoms.

11. The process according to claim 1 wherein at least one of $R_1$ to $R_8$ is phenyl.

12. A process for the hydrogenolysis of a compound represented by the structural formula I or II to give a compound represented by the structural formula III or IV and which does not require use of corrosive media comprising reacting I or II with hydrogen in the presence of a catalyst system that is a solid catalyst which contains at least one metal from Group VIII and/or Group IB of the Periodic System of Elements on a support consisting of at least one solid acid with an acid activity index of at least 90%, said acid activity index determinable by passing a gas stream consisting of 5 vol. % isopropanol and 95% vol. % helium through 100 grams of catalyst particles of a size range of 0.5 to 2.0 mm and with a flow rate of 50 ml/minute to thereby decompose said isopropanol to propene and water and then measuring the degree of conversion of isopropanol at 250° C., wherein the substituents $R_1$ to $R_8$, are the same or different, and are each a member selected from the group consisting of hydrogen alkyl, substituted or non-substituted aryl, hydroxyl, alkoxy, substituted or non-substituted aryloxy, halogen, carboxyl, a carboxylic acid derivative group, acyloxy, nitro, a sulphonic acid, mercapto, amino, alkyl-substituted amino and substituted or non-substituted aryl-substituted amino.

13. The process according to claim 12 further comprising the catalyst additionally containing a promoter selected from the group consisting of Sn, Ge, Pb and In.

14. The process according to claim 12 wherein said metal is present in an amount of 0.01 to 90% by weight based on the weight of the catalyst.

15. The process according to claim 12 wherein said support is a member selected from the group consisting of (a) an amorphous mixed oxide containing silicon and aluminum and (b) a crystalline compound based on Si, Al and O.

16. The process according to claim 15 wherein the support is an amorphous mixed oxide with a $SiO_2/Al_2O_2$ molar ratio of 99:1 to 1:99.

* * * * *